United States Patent [19]
Carlson et al.

[11] Patent Number: 5,594,375
[45] Date of Patent: Jan. 14, 1997

[54] ELECTRICAL POWER AMPLIFIER FOR CONTINUOUS CARDIAC OUTPUT MONITORING

[75] Inventors: Gary Carlson, Newport Beach; Jeffrey A. Norris, Lake Forest, both of Calif.

[73] Assignee: Baxter International Inc., Deerfield, Ill.

[21] Appl. No.: 466,544

[22] Filed: Jun. 6, 1995

Related U.S. Application Data

[62] Division of Ser. No. 268,217, Jun. 29, 1994.

[51] Int. Cl.⁶ .................................................. H03K 4/94
[52] U.S. Cl. ...................... 327/129; 330/207 A; 330/251
[58] Field of Search ............................ 327/129; 330/251, 330/207 A

[56] References Cited

FOREIGN PATENT DOCUMENTS 405090847  4/1993  Japan ..................................... 330/251

Primary Examiner—Margaret Rose Wambach
Attorney, Agent, or Firm—Bruce Canter

[57] ABSTRACT

A continuous cardiac output monitor includes a general-purpose monitoring console with local display and communication facilities, and a module removably interfacing with the console to configure the latter for performing continuous cardiac output monitoring. The module includes a switch-mode high efficiency power amplifier for providing electrical heating power at a selected voltage, frequency, and wave form to a heating element of a continuous cardiac output monitoring catheter, which catheter at a distal end portion thereof is immersed in the blood flow of a patient. The catheter effects a temperature transient in the patient's blood flow by the controlled application of electrical resistance heating utilizing electrical power from the power amplifier, and this temperature transient is sensed and used to derive a value for the patient's cardiac output.

2 Claims, 8 Drawing Sheets

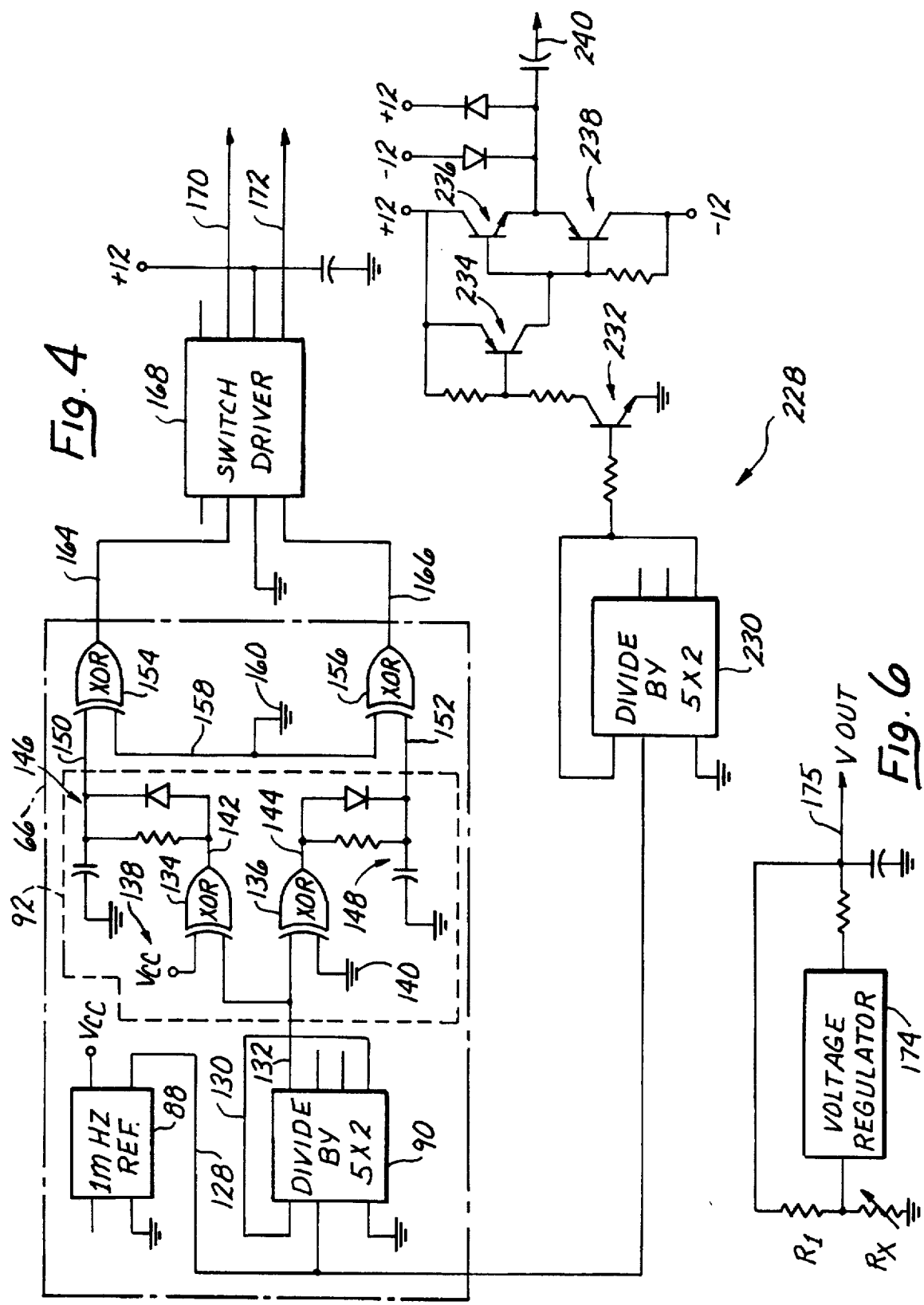

Fig. 5a
Fig. 5b
Fig. 5c
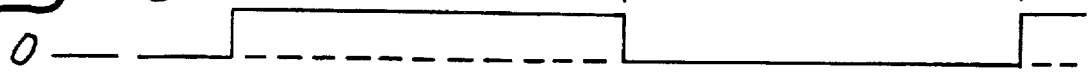
→ t
Fig. 5d
Fig. 5e
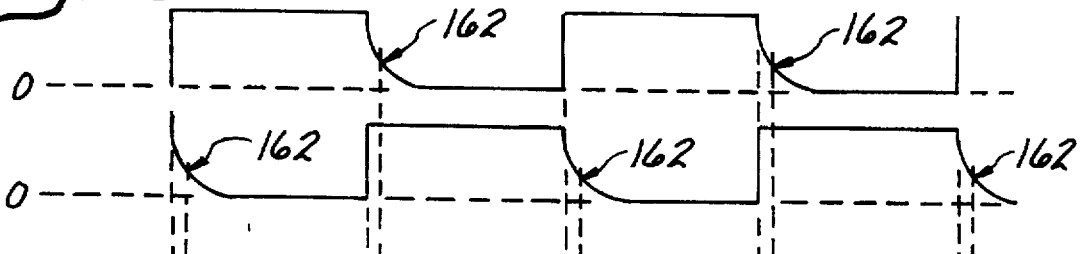
Fig. 5f
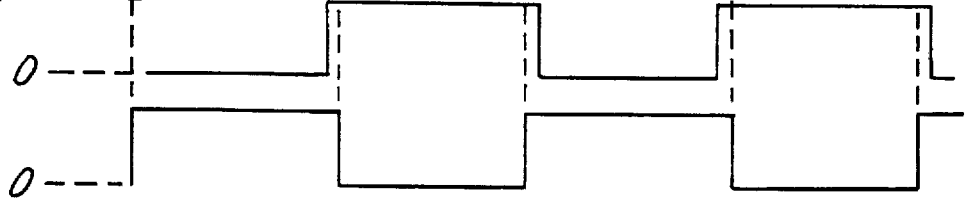

ELECTRICAL POWER AMPLIFIER FOR CONTINUOUS CARDIAC OUTPUT MONITORING

RELATED CASES

This application is a divisional of co-pending U.S. application Ser. No. 08/268,217, still pending filed on Jun. 29, 1994.

BACKGROUND OF THE INVENTION

1. Field of the Invention

The present invention relates to power amplifiers or electrical power supplies. More particularly, the present invention is in the field of power amplifiers for supplying electrical power at a chosen frequency or frequencies and at a selected and variable voltage level or levels. Still more particularly, the present invention is in the field of regulated electronic power amplifiers or supplies which supply a selected level of electrical power at a controlled frequency and variably controlled voltage to an electrical load. With particularity to the application environment of such power amplifiers or power supplies, the present invention relates to such a power amplifier which is particularly configured and constructed for use in the medical environment to supply resistive heating power to a continuous cardiac output monitoring catheter. Thus, the present invention also is in the field of apparatus and method for monitoring the cardiac output of a human patient.

2. Related Technology

Conventionally, cardiac output monitoring for patients experiencing a cardiac crisis, such as may occur over a period of time following a coronary occlusion, is to periodically inject a quantity (or bolus) of chilled saline solution into the patient's circulatory system at a selected location. A temperature monitoring catheter is used at another selected location to sense the temperature-versus-time relationship of the blood flow so that a value of cardiac output can be derived. This technique is known as thermodilution, and provides a good signal to noise ratio of the pulmonary blood flow as it is cooled by the chilled saline solution as compared to the normal temperature of blood flow in the pulmonary artery prior to and after the injection of the bolus of saline. A relationship known as the Stewart-Hamilton equation is used to derive the cardiac output value.

Unfortunately, this conventional technique is dependent on the skill of the person who performs the saline injection. That is, the rate and uniformity over time with which the bolus of saline solution is injected can influence the accuracy of the result. Consequently, a number of such tests over a period of time are used to determine an average value of cardiac output. Detection of a trend or long-term change (over a period of hours, for example) in cardiac output is very difficult with this conventional technique. Also, the injection of chilled saline may have the disadvantage for some patients of adding a relatively large quantity of water to the blood stream. This water must be removed by the patient's kidneys.

Another conventional cardiac output monitoring technique utilizes a catheter instilled through the right atrium and right ventricle of the heart, and from the heart into the pulmonary artery. A resistance heating element externally carried by this catheter is used to intermittently slightly heat the pulmonary blood flow from the heart as this blood flows toward the patient's lungs. Downstream of the heating element, the catheter carries a temperature sensing element. The temperature-versus-time relationship of the sensed blood flow can similarly be used to derive a value for cardiac output. This technique has the advantage of providing substantially continuous monitoring of cardiac output. However, the signal-to-noise ratio of the heated blood temperature in comparison to the normal body temperature of blood flow existing prior to and after an interval of heating is very low. This must be the case because the blood cannot be heated excessively or damage will result to formed blood cells. Consequently, techniques have been developed to heat the pulmonary blood flow on a pseudo-random basis, so that the resulting temperature variations can be detected and distinguished from the otherwise normal slight variations in temperature of the pulmonary blood flow.

For reasons of patient safety and avoidance of electromagnetic interference with or effect upon other monitoring and treatment apparatus which may also be in the medical environment around a patient, a frequency of 100 KHz has been recognized as the most desirable for use in powering the resistance heating element of the monitoring catheter. With this fixed frequency of applied power for the resistance heating element of the catheter, a variable voltage level is used to control the power level of energy liberated at the heating element into the patient's pulmonary blood flow. This control on the level of heating energy liberated into the patient's blood flow must be carefully controlled because the actual rate of blood flow circulation for the patient may be decreased or impaired, so that overheating must be avoided.

In addition to the above, it is increasingly recognized that the modern medical environment is restrictively complex. That is, the complexity of medical monitoring and treatment apparatus which must be used with some seriously ill or injured patients restricts access to the patient and presents the risk of error or malfunction of the apparatus. Additionally, hospitals and clinics face a significant burden in maintenance, service, storage, and logistical planning of the availability of this complex and expensive medical apparatus. As a result, an increasingly popular trend in the hospital, clinical, and portable medical treatment environments (fire departments, emergency medical teams, and military portable field hospitals, for example) is to use a general purpose monitoring device which can be electronically configured to serve a variety of monitoring functions.

Configuration of the monitoring device is accomplished by simply plugging into the console of the general purpose monitoring device one or more modules containing the circuitry and stored information necessary to accomplish particular monitoring functions. In the hospital and clinical environment, for example, this technology has the advantage that the general purpose monitors may be installed in or left in the patient rooms and in the emergency or critical care areas, for example. These monitors need not be moved about the hospital or clinic. The monitors are simply configured to perform various monitoring functions as are necessitated by the condition of the particular patient by plugging the appropriate modules into the monitor consoles. Only the modules need to be moved about the hospital or clinic. The modules themselves are comparatively small, light and inexpensive. Storage of the modules when they are not in use requires far less space than does the conventional monitoring equipment. Also, movement of the necessary configuration modules about the hospital or clinic environment does not present nearly the burden for hospital staff as does the movements of conventional monitors.

That is, conventional monitors are relatively large, heavy, and expensive pieces of equipment, which are generally mounted on wheeled carts. Each time a monitor is moved from one location to another within a hospital, for example, there is a certain risk that it will be damaged in the process of movement. Also, the physical movement of the monitor requires the services of a relatively strong member of the hospital service personnel, for example, to move the wheeled cart and monitor onto and off of hospital elevators. On the other hand, the configuration modules of modular type monitoring equipment are small enough to be carried by hand from one location to another. In fact, several of these modules can be carried at a time by one person if necessary. A single wheeled cart of a size comparable to one conventional monitor can carry several to several dozen of the configuration modules for a modular monitoring system.

With respect to the conventional continuous cardiac output monitors, the monitor includes a linear electronic power amplifier capable of supplying a variable power level and fixed frequency of electrical alternating current power output, and which provides electrical heating power to the resistance heating element of the continuous cardiac output monitoring catheter. This conventional linear power amplifier is physically too large to be accommodated within the envelope of a monitoring module of the newer modular-type of monitoring apparatus. Also, the conventional power amplifier is of a power efficiency so low that although only about fifteen watts of power is dissipated into the patient's blood flow on an intermittent basis, about thirty to forty-five watts, or more, of power is liberated as heat into the console of the conventional continuous cardiac output monitor. That is, the efficiency of these conventional linear power amplifiers may be as low as 25 percent. Were this level of heat to be liberated within a monitoring module, assuming that the conventional linear power amplifier could somehow be physically fitted into the module, the conventional plastic casing of the module could be warped or melted by the resulting high temperatures.

SUMMARY OF THE INVENTION

In view of the deficiencies of the related technology as explained above, an object for the present invention is to provide a power amplifier which avoids one or more of these deficiencies.

More particularly, an object of the present invention is to provide a power amplifier for a continuous cardiac output monitoring apparatus which allows the power amplifier to be physically fitted within a configuring module for a modular-type of monitoring system.

Still another object for the present invention is to provide such a power amplifier having such a high level of efficiency that a permissibly small level of heat energy is liberated from the power amplifier, allowing the power amplifier to be housed in a module compatible with conventional modular monitoring apparatus.

Particularly, the present invention relates to apparatus and method for electrically heating cardiac blood flow within the heart of a human patient, and for sensing the temperature versus time relationship of the blood flow in the pulmonary artery. The power amplifier provides alternating current electrical power at a particular frequency chosen because of the particular safety of this frequency for the patient, and relative freedom of this frequency from the production of electromagnetic interference which could affect other medical apparatus being used in the treatment of the patient. The alternating power supplied is of variable voltage level to control the energy dissipated in a resistive load from which heat energy is applied to cardiac blood flow. The heat energy is intermittently according to a pseudo random algorithm to provide a temperature transient in the patient's cardiac pulmonary blood flow, which transient is sensed in order to derive a value for cardiac output of the patient.

Accordingly, the present invention provides a cardiac output monitor for use with a cardiac output monitoring catheter immersed in the blood flow of a patient, the catheter having a heating element in heat transfer relation to the blood flow to provide a temperature transient therein in response to the controlled application of electrical resistance heating, and a temperature sensor disposed on the catheter down stream of the heating element in the blood flow for providing a response to the temperature transient, the monitor comprising a console having provision for connection with the catheter for supplying electrical power thereto and for receiving therefrom the response to the temperature transient in the patient's blood flow, the monitor further including an output device for locally displaying indicia relative to the cardiac monitoring of the patient, including a value for cardiac output; and a module removably attaching to the console, the module providing an electrical power amplifier circuit for selectively supplying electrical heating power of a selected frequency and voltage level to the console for connection through the console to the heating element of the catheter.

According to a further aspect, the present invention provides an alternating current switch-mode electrical power amplifier for supplying alternating current of a selected frequency; the power amplifier comprising a reference oscillator providing a reference asymmetrical pulse train signal having a frequency which is a multiple of the selected frequency; divider means for first dividing the reference pulse train by a value which is equal to the multiple divided by two to provide a resulting pulse train, and then dividing the resulting pulse train by two to provide a final square wave pulse train having a 50 percent duty cycle and which toggles between a first higher value and second lower value at the reference frequency; and switching means for switching electrical power alternatingly at the selected frequency in response to the final pulse train.

An advantage of the present invention resides in the freedom from harmonic interference in the regulated power supplied by the power amplifier. That is, such harmonic interference frequencies are substantially not present at all in the alternating current power supplied by the present power amplifier. The present power amplifier supplies essentially pure sine wave alternating current electrical power. Further, the small size, light weight, low cost, frequency stability, fault tolerance (actually, redundant fault tolerance), and good accuracy of the power level regulation provided by the present power amplifier are individually and in combination better than can be achieved with conventional power supplies.

Additional objects and advantages of the present invention will be apparent from a reading of the following description of a particularly preferred exemplary embodiment of the invention taken in conjunction with the appended drawing Figures, which are described below.

DESCRIPTION OF THE DRAWING FIGURES

FIG. 1 provides a fragmentary and somewhat schematic view of a human patient having a continuous cardiac output monitoring catheter instilled into the pulmonary artery, and a modular monitoring apparatus associated with this catheter.

FIG. 2 schematically depicts the functional components of the present continuous cardiac output monitoring apparatus in association with a section of a cardiac output monitoring catheter which is instilled into a patient's pulmonary artery, and illustrates the functional relationship of these components.

FIG. 3 depict, a power amplifier of the present invention.

FIG. 4 presents a schematic and functional block diagram of the components and interconnections of these components for a power amplifier embodying the present invention.

FIGS. 5a–5c present voltage wave forms at selected locations in the power amplifier seen in FIG. 4, with these wave forms set out on a common time scale.

FIGS. 5d presents a resulting voltage wave form resulting from the wave forms seen in FIGS. 5a–5c, and with the time scale compressed to allow depiction of several voltage wave form cycles.

FIGS. 5e and 5f show further resulting voltage wave forms which are shown on a slightly expanded time scale and with an expanded voltage amplitude scale as well.

FIGS. 6–11 provide fragmentary views of a power amplifier electrical circuit embodying the present invention.

DETAILED DESCRIPTION OF AN EXEMPLARY PREFERRED EMBODIMENT OF THE INVENTION

Figure 1:
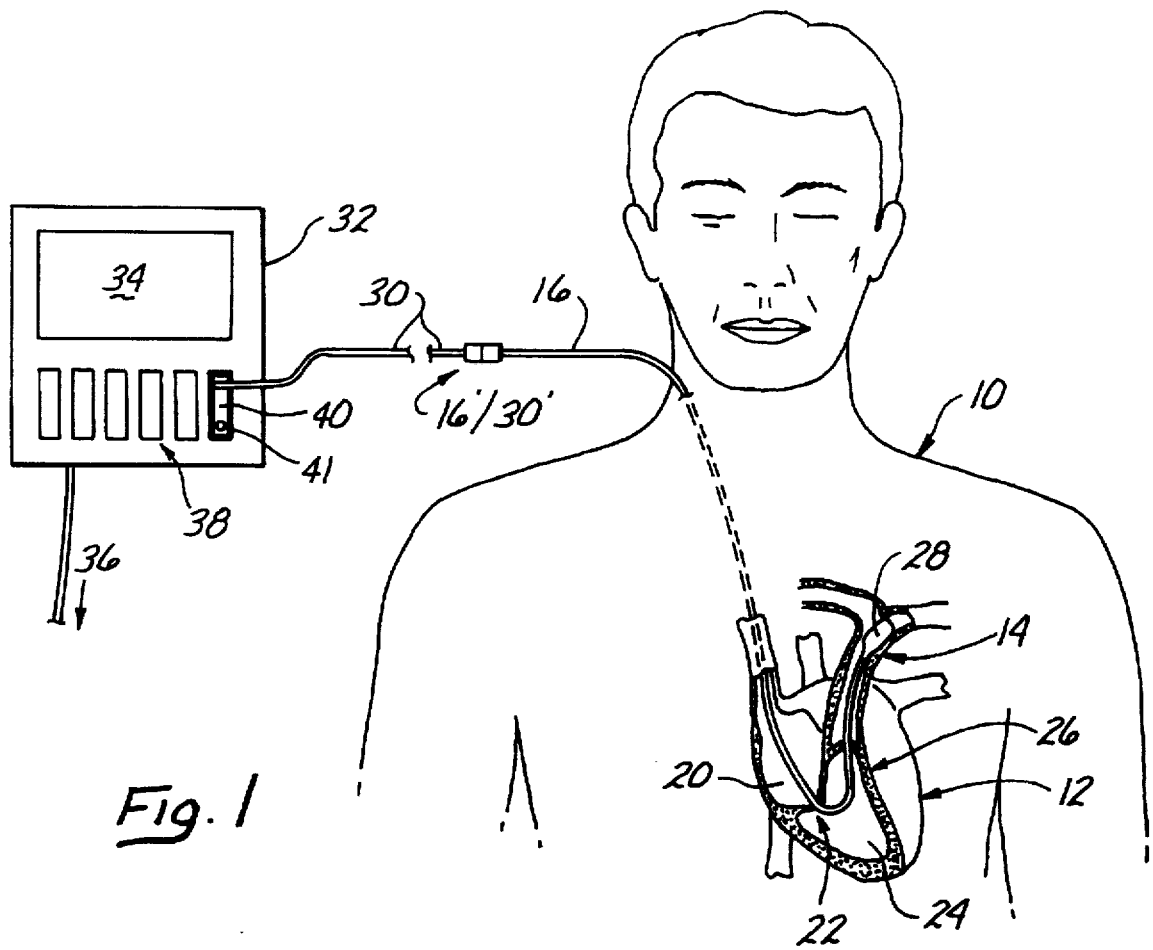

FIG. 1 shows a human patient 10, who, for example, may have suffered a coronary occlusion or heart attack, or who may have suffered severe trauma such as may occur from a motor vehicle accident. For the heart attack patient, because damage to the patient's heart 12 occurs not only as a result of an initial occlusion, or blockage of a coronary artery, but also over a period of several hours or several days as portions of the patient's heart become necrotic as a result of the occluded coronary blood supply, the patient's coronary capacity is at risk of failure over this considerable time period following the heart attack. For the trauma patient, who may have lost a considerable quantity of blood, and who may be in shock, dilation of peripheral vasculation of the body may result in a decrease in blood pressure while the coronary capacity of the patient is decreased over a period of time. During these time periods, early detection of an impending heart failure is very important so that early interventional measures can be taken while these measures can have their best effect.

Experience has shown that monitoring of the patient's blood pressure alone, or monitoring of blood oxygen saturation levels at the extremities of the patient 10, for example, are not adequate indications of impending heart failure. As a result, conventional technology has been developed which effects a monitoring of the patient's pulmonary blood circulation, as well as other related factors, such as oxygen saturation of the blood flowing to the patient's lungs, directly at the pulmonary artery 14 of the patient 10.

This monitoring of pulmonary blood flow is effected by instilling a monitoring catheter 16 into the patient's right jugular vein. A distal end portion 18 of this catheter is advanced down the vein into the right atrium 20 of the heart 12. From the right atrium 20, the distal end portion 18 is advanced through the tricuspid valve 22 and into the right ventricle 24 of the heart 12. Subsequently, the distal end portion 18 of the catheter 16 is advanced through the pulmonary valve 26 and into the pulmonary artery 14. As those who are ordinarily skilled in the pertinent arts will appreciate, usually, an inflatable balloon portion 28 of the catheter 16 will be inflated for this introduction procedure so that the prevailing blood flow helps in moving or floating the catheter along to its desired location.

Externally of the patient 10, the catheter 16 is connected at a plug-and-socket interface 16'/30' to a multi-conductor electrical cable 30. This cable 30 provides similar plug-and-socket connection to electrical circuitry located at a general purpose variably-configurable modular-type of monitor console 32. This monitoring console 32 includes a display screen 34 upon which information about the patient's condition can be locally displayed. Also, this monitor 32 includes a data output facility, such as a computer system RS-232 port (schematically indicated with the arrowed numeral 36), and by which patient information is provided to a remote location, such as to a nurse's station, central patient monitoring and data recording computer system, or to a physician who may wish to receive the information at his home or office via a telephone line interconnection with such a hospital's central patient monitoring computer system.

The console 32 includes a plurality of electrical interconnection apertures or ports 38 into which configuration modules may be received in order to configure the monitor to perform those monitoring functions which are required by particular patients. In the present case, the console 32 has received a module 40 for monitoring cardiac output of the patient 10. The cable 30 has direct plug-and socket connection to the module 40, which provides interface between the catheter 16 and the console 32. The module 40 includes a second cable connector 41 which is configured to receive the connector 30' at the distal end of the cable 30 where catheter 16 connects for monitoring of the patient 10. As will be seen, the module 40 can also be used to verify the correct operation of the cable 30 by connection of both ends of the cable 30 to the module 40.

Figure 2:
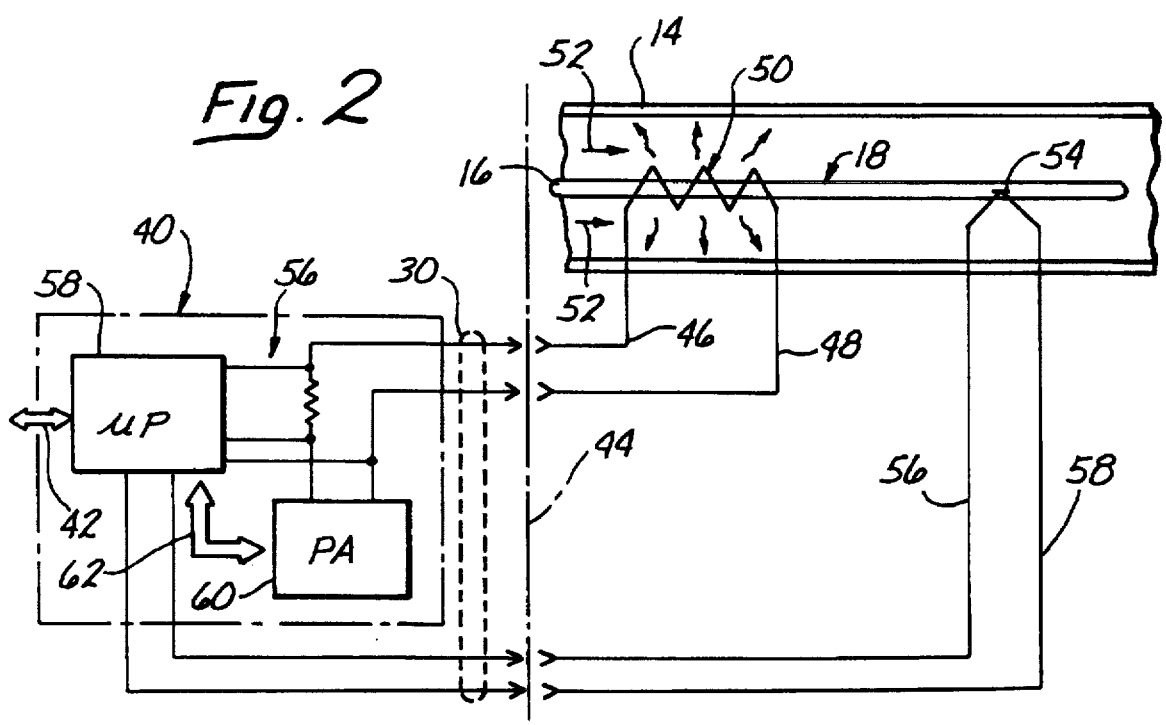

With attention now to FIG. 2, it is seen that the module 40 has connection to the monitor 32 via a data bus, generally indicated by the double-headed arrow 42, and via a number of electrical connections which supply electrical power to the module 40 from the console 32. It will be appreciated that FIG. 2 is very schematic, and that the electrical conductors depicted outwardly of catheter 16 are actually of a fine gauge and over a portion of their length are disposed within the elongate and comparatively thin shaft of the catheter. Another portion of the length of the illustrated conductors will be understood to be provided by the cable 30. Two of the conductors 46 and 48 connect to a resistance heating element 50 which is outwardly disposed on the distal end portion 18 of the catheter 16. The heating element 50 may actually be configured as a flexible thin metallic film element having a high coefficient of resistance change with change in temperature.

The catheter 16 will preferably be configured so that this heating element 50 is actually disposed in the right ventricle of the patient 10. The turbulent blood flow in this ventricle resulting from the pumping action of the heart assists in distributing heat energy from the heating element 50 uniformly throughout the pulmonary blood flow. Downstream of the heating element 50 with respect to the direction of blood flow (indicated with arrows 52) is disposed a temperature measuring sensor 54. The sensor 54 may be a small bead thermistor, for example, and is connected to the cable 30 and console 32 via conductors 56 and 58. Within the module 40, the conductors 56 and 58 supply the temperature signal from sensor 54 to a microprocessor based control system 56, including a microprocessor 58 and power amplifier circuit 60. The microprocessor 58 has a two-way control and data interface with the power amplifier circuit 60, as is generally indicated by the control and data bus arrow 62. This general interface reference numeral (62) is used throughout the following explanation to refer to the interface of information and control signals in one or both directions between the power amplifier 60 and the microprocessor 58.

Figure 3:
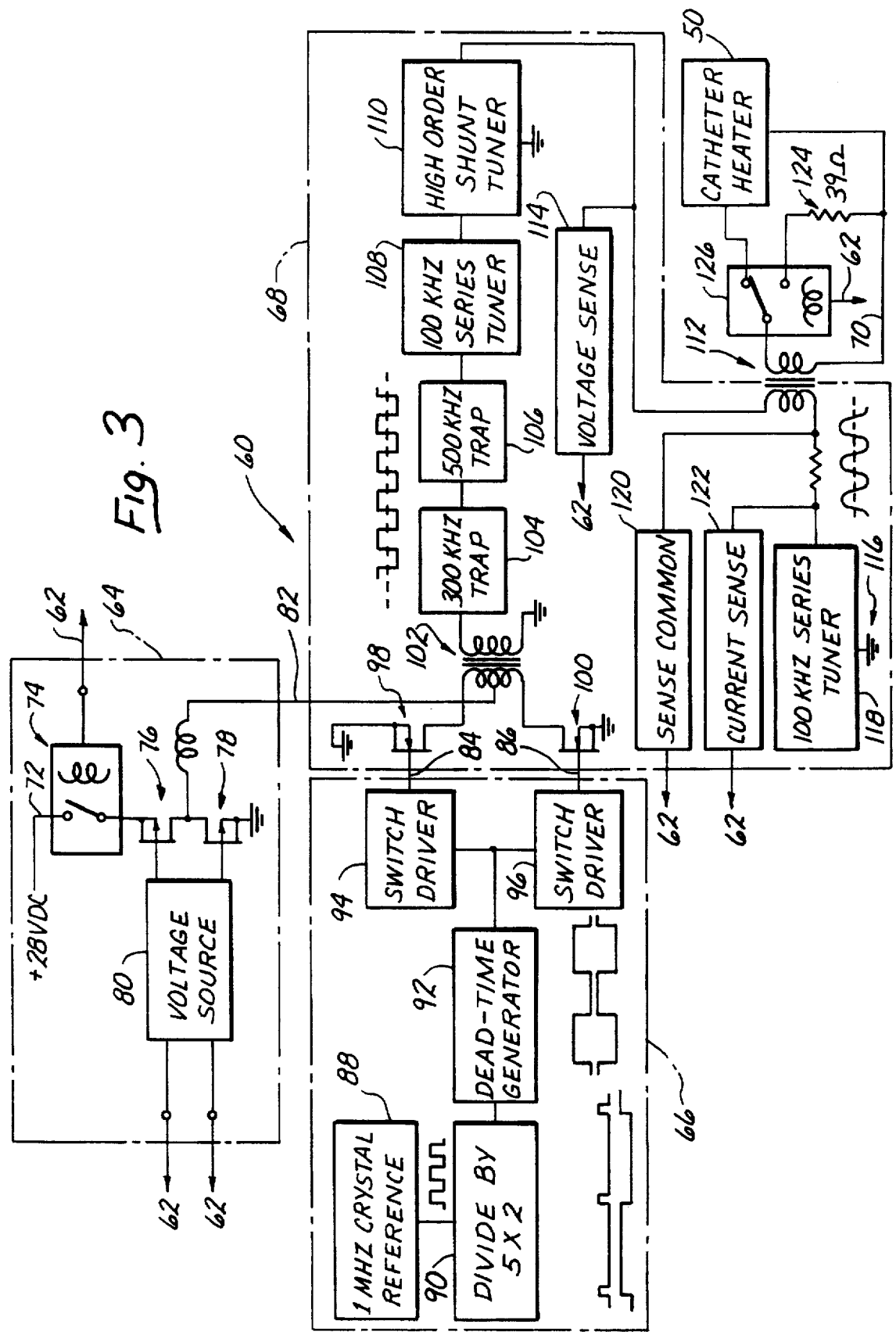

FIG. 3 shows that the power amplifier 60 includes a programmable selectively variable voltage source section 64, a frequency source section 66, and a switch-mode amplifier section 68 which receives as inputs both electrical power at a selected programmable voltage level from the section 64, and a reference frequency signal from the section 66, and which combines these inputs to provide frequency-controlled alternating current electrical power to an isolated patient-connected section 70 with a pure sine wave form at a selected and variable voltage level. Electrically, the patient-connected section 70 is defined in part by the catheter 16 and the cable 30. The programmable selectively variable voltage source 64 has connection, as is depicted at 72, to a 28 volt direct current power source (not shown). A power cut off relay 74 is under the control of the microprocessor 58, as is indicated by the interface connection 62. As will be seen, this control of relay 74 by microprocessor 58 is redundant, and is further backed up by control of the voltage source 80 by the microprocessor 58 so that the relay 74 can be opened or voltage source 80 may be commanded to provide a zero output voltage, all in order to safeguard the patient 10 from inadvertent injury by excessive heating at catheter 16. This relay 74 supplies electrical power to a pair of semiconductor switches 76 and 78. Switches 76 and 78 are controlled by a voltage regulator circuit 80, which is also under the control of the microprocessor 58, as is indicated by the interface connections 62.

As will be further explained below, the applicants have adapted a conventional semiconductor integrated circuit voltage regulator, which is designed to provide a steady regulated voltage output level even if its supply voltage varies, and have created a programmable selectively variable direct current voltage supply. In the present case, the programmable voltage supply has a resolution of $2^{12}$, or 4095 different incremental voltage levels which may be individually selected by the microprocessor 58 in order to control the level of resistance heating and energy dissipation at the heating element 50 of catheter 16. Accordingly, the level of electrical power which is supplied by the module 40 to the heating element 50 of the catheter 16 is under very fine control by the microprocessor 58.

Direct current electrical power of finely controlled voltage level is supplied by the voltage source section 64 to the amplifier section 68, as is indicated by the schematic conductor 82. The power amplifier section 68 also receives a precisely regulated frequency signal from the frequency source section 66, as is indicated by the schematic conductor connections 82 and 84. As can be seen from the schematic illustration of FIG. 3, the frequency source section 66 includes a 1 MHz crystal reference oscillator 88. This oscillator 88 provides an asymmetrical (i.e., positive-going only) output signal at a precise 1 Mhz rate with a high-signal duty cycle of about 40 percent. This signal is provided to a divider circuit 90, which first effects a division by 5 to provide a 200 KHz signal, which is still only positive going, and has a low duty cycle. As an aid to the reader at this point in the circuit description, small graphical signal wave-form illustrations have been added to FIG. 3.

Next, the divider circuit 90 effects a division by 2 to provide a 100 KHz signal which toggles between a signal-high value and signal-low (zero) value 100 thousand times a second. While this signal is a square wave form and is only positive-going, it is the basis for a pure symmetrical alternating current wave form which will be provided by the power amplifier 60. As those who are ordinarily skilled in the pertinent art will be aware, a pure square wave form of 50 percent duty cycle has only odd-factored harmonics added to a pure sine wave form when analyzed by Fourier analysis. As will be seen, the wave form provided by the divider 90 is used to effect a switching of direct current into a pure square wave form from which the odd-factored harmonics are removed, to provide a pure sine wave form of alternating current output from the power amplifier 60. In order to prevent simultaneous conduction, and a resulting short circuit, during switching of the direct current power from the voltage source section 64, a dead-time generator is provided to provide a pair of oppositely-going square wave signals which still have a 50 percent duty cycle. These signals are provided to respective ones of a pair (94, 96) of switch drivers. These switch drivers 94, 96 in turn control switching of respective ones of a pair of semiconductor (MosFet) switches 98, 100, which are part of the power amplifier section 68.

Considering now the power amplifier section 68, it is seen that the switches 98, 100 control current flow through opposite sides of a center-tapped transformer 102. Preferably, this transformer has a turns ratio of substantially 1:1.6 As mentioned above, this center tapped transformer 102 provides a square wave output at a frequency of 100 KHz with a 50 percent duty cycle. Consequently, this square wave has the characteristics of a pure sine wave with only odd-numbered harmonic factors added. Power amplifier section 68 includes first and second series tuned circuits 104 and 106, which are respectively tuned to present a very high impedance to the third and fifth harmonic factors of the 100 KHz signal from transformer 104. That is, circuit 104 is tuned to present a very high impedance so as to effectively block the 300 KHz component of the signal from transformer 102, while the circuit 106 is tuned to block the 500 KHz component. This blockage of the third and fifth harmonic components of the selected frequency signal from the transformer 102 is an important aspect of the present power amplifier because these first two odd-numbered (third and fifth) harmonics carry the most energy. By presenting a high impedance at the circuits 104 and 106, a large portion of this energy of the third and fifth harmonics will be reflected and will not be lost to inefficiency in the power amplifier 60.

Next, the power amplifier section 68 includes a series tuned circuit 108, which presents a very low impedance to the 100 KHz selected frequency, while presenting a high impedance to higher order harmonic frequencies of the 100 KHz selected frequency. The remaining portions of the higher order harmonics which pass the tuned circuit 108 are shunted to ground by a high-order shunt tuner circuit 110. This shunt tuner. circuit 110 drives a resulting sine wave voltage signal into the primary winding of an isolation transformer 112 having a turns ratio of substantially 3:1. As is seen on FIG. 3, a voltage sensing circuit 114 is associated with the connection between the shunt tuner circuit 110 and the primary winding of the transformer 112 in order to provide a feed back value of voltage supplied to the catheter 16 to the microprocessor 58, as is indicated by the interface arrow 62.

Importantly, the ground side of the transformer 112 is connected to the ground indicated at 116 via a second 100 KHz series tuner circuit 118. The series tuned circuits 108 and 118 are separated from one another by the high reflected impedance appearing at the primary winding of the isolation transformer 112 by virtue of its 3:1 turns ratio so that the inductances and capacitances of these tuners do not simply add with one another to result in a composite tuned circuit which would have a tuned frequency other than 100 KHz. Accordingly, the tuned circuits 108 and 118 can each participate in insuring that substantially only a pure sine wave voltage form at 100 KHz is effective at the primary winding of transformer 112. FIG. 3 also shows that the power amplifier section 68 of power amplifier 60 has connection to the microprocessor 58 via a sense common circuit 120, and a current flow sensing circuit 122.

The isolated patient-connected circuit section 70 effectively floats with respect to ground potential because no ground connection is made across the isolation transformer 112. This isolated patient-connected section 70 of the power amplifier circuit 60 includes the resistive heating element 50 of the catheter 16, and a calibration resistor 124. Each of these resistances has a value of substantially thirty nine ohms, so that the reflected impedance at the primary winding of the isolation transformer is substantially 350 ohms (i.e., 39 ohms multiplied by the square of the turns ratio across transformer 112). Also, isolated patient-connected circuit section 70 includes a relay 126 switching the connection of the secondary winding of transformer 112 between the heating resistor 50 and the calibration resistor 124. This switching relay 126 has a connection with the microprocessor 58, as is indicated with interface arrow 62. Accordingly, the microprocessor 58 can not only control the condition of relay 126, but can also verify this condition (as will be further explained), so that the microprocessor 58 can verify that electrical power is applied to the heating resistor 50 only when commanded by the microprocessor 58, and cannot be applied otherwise without the microprocessor taking positive action to shut down the entire module 40.

Considering now FIG. 4, a more greatly detailed presentation of the frequency source circuit section 66 is presented. This circuit section includes the crystal oscillator 88, which provides the square wave positive-going signal seen in FIG. 5A to the divider 90 via a conductor 128. Divider 90 effects first a division by five to produce the signal seen at FIG. 5B. This signal varies between zero and a positive value upon each fifth positive-going signal transition of the signal seen in FIG. 5A. The value of the signal seen in FIG. 5B drops back to zero after a comparatively short time interval, which is considerably shorter than the time required for five cycles of the signal of FIG. 5A to pass. Importantly, the signals seen in FIGS. 5A and 5B are not square waves with a 50 percent duty cycle, and will not satisfy the relationship explained above with respect to having only odd-ordered harmonics with respect to a pure sine wave signal. The signal seen in FIG. 5B is output by circuit 90 on a conductor 130, which returns this signal to the circuit 90 to a terminal at which a division by two is effected. The division by two results in a signal seen in FIG. 5C which toggles between zero and a positive value at a rate of 100 KHz. This signal is a square wave with a 50 percent duty cycle, but is positive-going only. That is, the signal of FIG. 5C is not symmetrical about the zero voltage axis.

This signal of FIG. 5C is provided by a conductor 132 to the dead time generator circuit 92. This circuit 92 includes a pair of oppositely-connected exclusive-OR (XOR) gates 134, and 136. The gate 134 is connected at one input terminal to the positive input $V_{cc}$ (indicated with the numeral 138), and at the other input terminal receives the signal of FIG. 5C.

Consequently, the gate 134 conducts only while the signal of FIG. 5C is positive. On the other hand, the gate 136 is connected at one input terminal to the signal of FIG. 5C, and at the other input terminal is connected to ground (indicated with the numeral 140). This gate 136 consequently conducts only while the signal of FIG. 5C is zero. The result is that the gates 134 and 136 each provide respective ones of a pair of time-matched square-wave signals which are positive-going only, and are oppositely time sequenced, as is seen in FIG. 5D. The reader will note that the time scale of FIG. 5D is considerably compressed in comparison to that of FIGS. 5A through 5C, so that several cycles of the time-matched oppositely-sequenced signals can be shown. These signals of FIG. 5D are provided on respective conductors 142 and 144 to respective resistor-capacitor networks 146 and 148, each one of which also includes a respectively oriented diode conducting toward ground potential so that the signal provided by the gates 134 and 136 can transition high to charge the capacitor (as seen on a respective conductor 150 and 152), but can transition low only with the added effect of the resistor-capacitor time constant resulting from the networks 146 and 148. The resulting signals at the conductors 150 and 152 are seen in FIG. 5E. These signals are still only positive-going, and between the two signals have a duty cycle of 50 percent.

The signals of FIG. 5E are provided to a pair of exclusive-OR gates 154 and 156, which are connected together at one of their input connections by a conductor 158. The conductor 158 has a ground connection, indicated by numeral 160. Consequently, the gates 154 and 156 each individually only conduct when the signal received from the conductors 150 and 152 (the signal of FIG. 5E) are high. However, these gates do not switch off as soon as the signal of FIG. 5E drops below it greatest high value. Instead, these gates switch off at some voltage level intermediate of the high and low (zero) signal levels. Because of the resistor-conductor time constants effective on the zero-going portion of the signals seen in FIG. 5E, the gates 154 and 156 do not switch off simultaneously with the signals seen in FIG. 5D, but have their switching off delayed until some lower but non-zero voltage value, indicated with the numeral 162 is reached. As a result, the gates 154 and 156 provide on respective conductors 164 and 166 respective signals as are indicated in FIG. 5F. These signals are still only positive-going, and have a 50 percent duty cycle between the two of these signals. However, the switching-off transition (i.e., the negative going part of the square wave form) of each wave form is delayed slightly with respect to the positive-going transition of the companion wave form seen in FIG. 5F. Conductors 164 and 166 provide the signals seen in FIG. 5F to a switch driver circuit 168, which inverts each of these signals so that the positive-going turn-on part of the signal is delayed with respect the negative-going turn-off portion of the signal. The switch driver circuit 168 provides respective inverted signals of the same wave form as is seen in FIG. 5F, but of respectively inverted shape and transposed time sequencing, on conductors indicated with the numerals 170 and 172. The use made of these signals with be further explained below.

Figure 7:
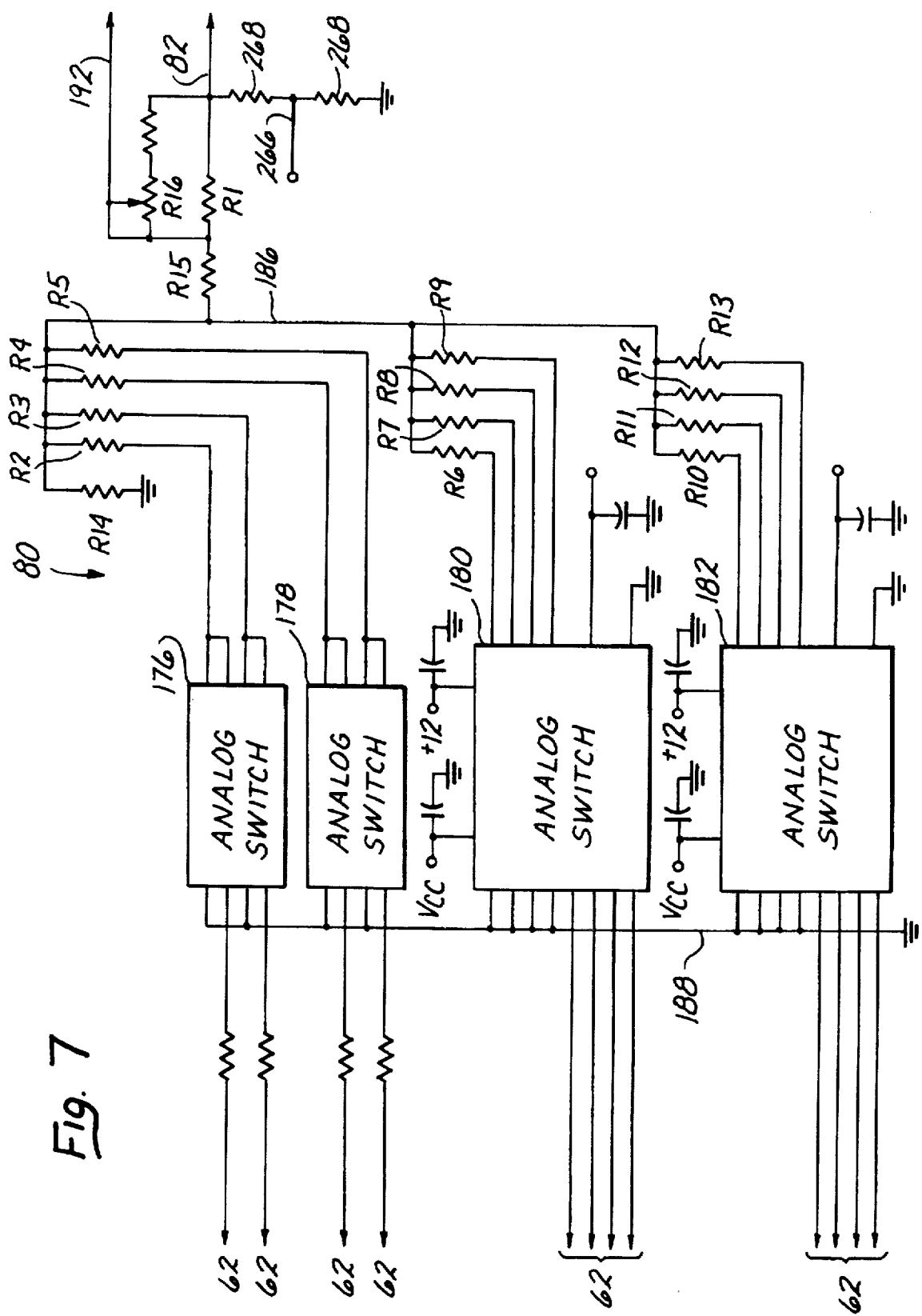
Figure 8:
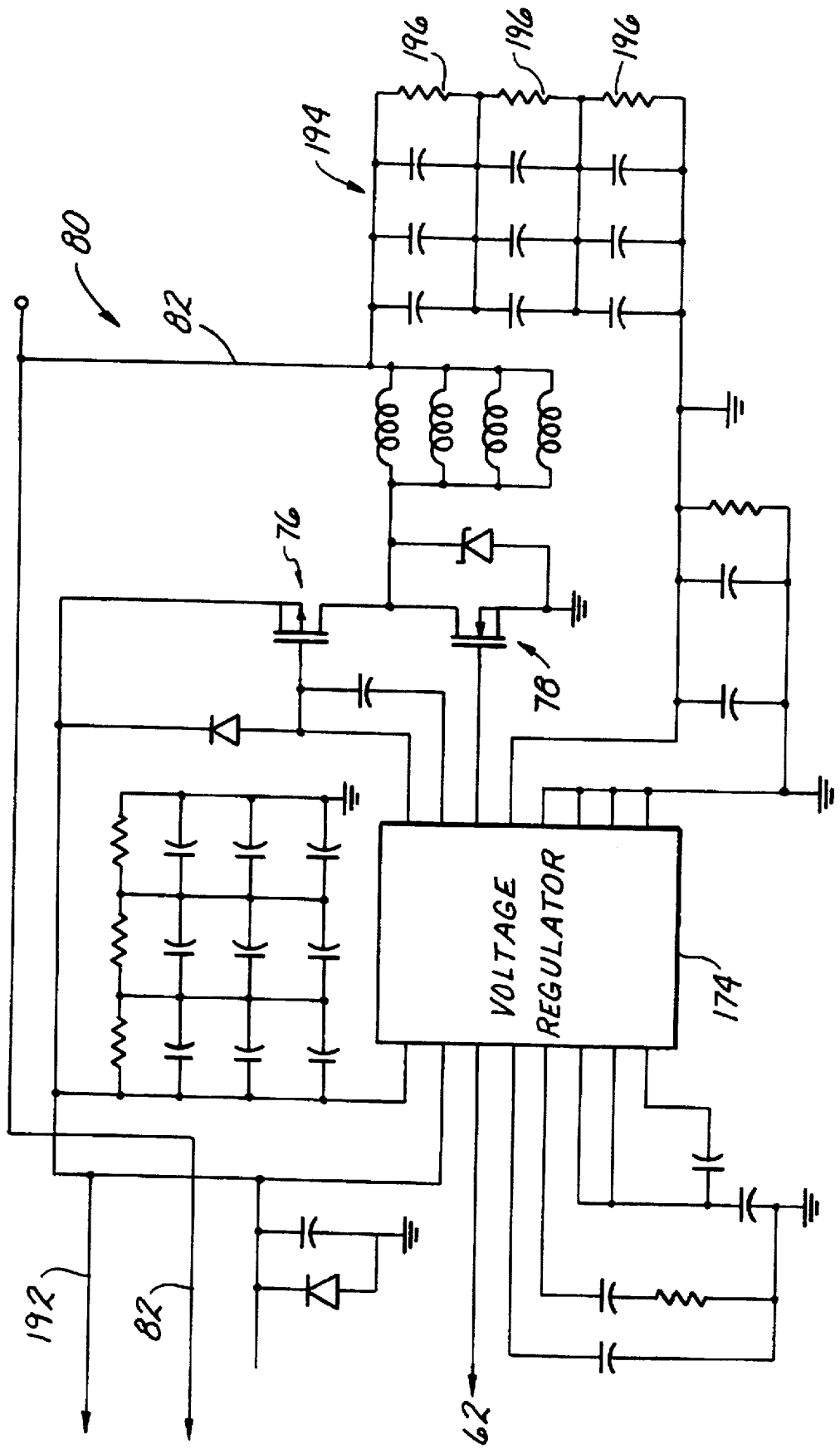

Viewing now FIGS. 6-8 in conjunction with one another, the voltage regulator 80 and switches 76, 78 of the programmable selectively variable voltage source circuit 64 of FIG. 3 is shown in greater detail. Particularly, FIG. 6 schematically depicts the overall circuit schematic for a regulated voltage supply using a voltage regulator integrated circuit 174. This circuit 174 provides an output voltage on a conductor 175 which is equal to a constant multiplied by the sum of one plus the quotient of the value of resistor $R_1$ divided by the value of resistor $R_x$. According to the present preferred embodiment of the invention, this constant is 1.25. As is seen in FIG. 6, resistor $R_x$ is a variable resistor according the present invention. Further, as will be seen, the present invention includes provision for the value of resistor $R_x$ to be digitally programmable and to be controlled by microprocessor 58. The value of resistor $R_x$ is programmable with a resolution of $2^{12}$ incremental values. Accordingly, it will be seen that the regulated and controlled voltage level provided by the voltage regulator circuit 174 is controllable by the microprocessor 58 with a fine degree of control.

Turning now to FIGS. 7 and 8 in combination, it is seen that the voltage regulator circuit 80 includes a resistor designated $R_1$, which is seen in FIG. 8, and which functions as the resistor designated in the same way and seen in FIG. 6. The voltage regulator circuit and switches 76 and 78 are also seen in FIG. 8. Also, this voltage regulator circuit section includes an array of four digitally-controlled analog switches 176, 178, 180, and 182, which are seen in FIG. 7. The analog switches 176–182 are each controlled by the microprocessor 58 via the interface connections designated with the numeral 62, and seen along the left side of FIG. 7. That is, the microprocessor 58 can drive up the signal level at individual ones or groups of as many as all of the signal leads to these analog switches. A signal-high value on any one of the conductors indicated results in the associated switch 176–182 switching a respective one of the resistors indicated below into a parallel resistance relationship to ground.

To further explain the above, it is seen that the analog switches 176–182 also have connection individually with an array of twelve resistors, which are designated $R_2$ through $R_{13}$, and which are individually switched into connection with a grounded conductor 188 when the respective one of the leads indicated with the interface numeral 62 are driven signal-high by the microprocessor 58. These resistors $R_2$ through $R_{13}$ collectively function as the variable resistor $R_x$ seen in FIG. 6. These resistors have increasing values ranging generally from about 200 ohms to about 422 Kohms. Particularly, the resistors $R_2$ through $R_{13}$ have values in ohms of: 200, 402, 806, 1.62K, 3.24K, 6.49K, 13.0K, 26.1K, 52.3K, 105K, 210K, and 422K. An example of an analog switch which has proved to be acceptable for use as the switches 176 and 178 for switching the resistors having the lower values (i.e., in the range from about 200 ohms to about 1.6 Kohms, is the Siliconix 9956DY. This analog switch has a very low resistance when switched on. Thus, the resistance of the switches 176 and 178 themselves does not itself add appreciable to the resistances of the resistors $R_2$ through $R_5$. On the other hand, for the analog switches 180 and 182, a Harris DG412DY has shown to be acceptable. This analog switch has a very low leakage current when switched off so that the comparatively small incremental change in current flow which results when the higher-valued resistors $R_6$ through $R_{13}$ are switched in parallel into the circuit can be easily distinguished from the leakage current through the switches 180 and 182 themselves. The resistors $R_6$ through $R_{13}$ have values greater than 1.6 Kohm, up to or greater than about 422 Kohm. Preferably, the resistors $R_2$ through $R_{13}$ are precision 0.1 percent, 50 PPM resistors in order to enable closer calibration of the voltage supplied by the voltage regulator 174.

It will be noted viewing FIG. 7 that a resistor $R_{14}$ is provided to adjust the maximum resistance value appearing on conductor 190 along with a resistor $R_{15}$ and a trimming resistor $R_{16}$ adjusting the effective resistance appearing at conductor 192. The value of the resistor $R_{15}$ sets the maximum voltage which the voltage regulator 174 will supply even when all of the resistors $R_2$ through $R_{13}$ are switched to ground by closing of all of the analog switches 176–182. The conductor 192 appears at the left side of FIG. 8, and has connection with the voltage regulator circuit 174. This conductor 192 is analogous to the conductor schematically seen at the upper end of resistor $R_x$ of FIG. 6, and having connection with the regulator circuit 174. The effective resistance value to ground from conductor 192 controls the voltage level output by voltage regulator circuit 174. As is seen, the microprocessor 58 controls this effective voltage level by effecting switching of resistors $R_2$ through $R_{13}$ into connection with grounded conductor 188 via the analog switches 176–182. Also, the microprocessor 58 can control the voltage regulator circuit 174 through the indicated interface line 62 so that the voltage regulator 174 is turned off to provide no output power, or is turned on to provide output power of the voltage level selected by the switched condition of the analog switches 176–182. Accordingly, the microprocessor 58 can control the power level of electrical heating effected at the heating element 50 of the cathode 16 from zero to the full wattage capacity of this heater.

Viewing FIG. 8, another feature of the present voltage source circuit section will be seen. An example of an integrated circuit acceptable for use as the voltage regulator 174 is the Linear Technology LTC1149. This voltage regulator has a constant off time architecture, rather than a fixed switching frequency. Consequently, operating frequency of this voltage regulator will vary with output voltage. For the present application, the output voltage can vary between 1 volt and 26 volts DC. Recalling FIG. 6 it is seen that the voltage regulator circuit 174 requires a capacitance to ground connected in common with the conductor connecting to the reference resistor $R_1$. In order to avoid the use of large high-voltage capacitors and preserve the small size, weight, and cost goals of the present power amplifier, this capacitance is provided by a capacitor array indicated with the numeral 194 on FIG. 8. The capacitor array includes a plurality of capacitors connected between the conductor 82 (which is the regulated-voltage power output conductor for the selectively-variable voltage source circuit section 64, recalling the description of FIG. 3), and ground. The capacitor array 194 includes a number of equally valued resistors 196, which serve as voltage sharing resistors among the capacitors of the array 194, distributing the voltage drop equally across these capacitors and preventing an excessive current flow in any one of the capacitors.

Figure 9:
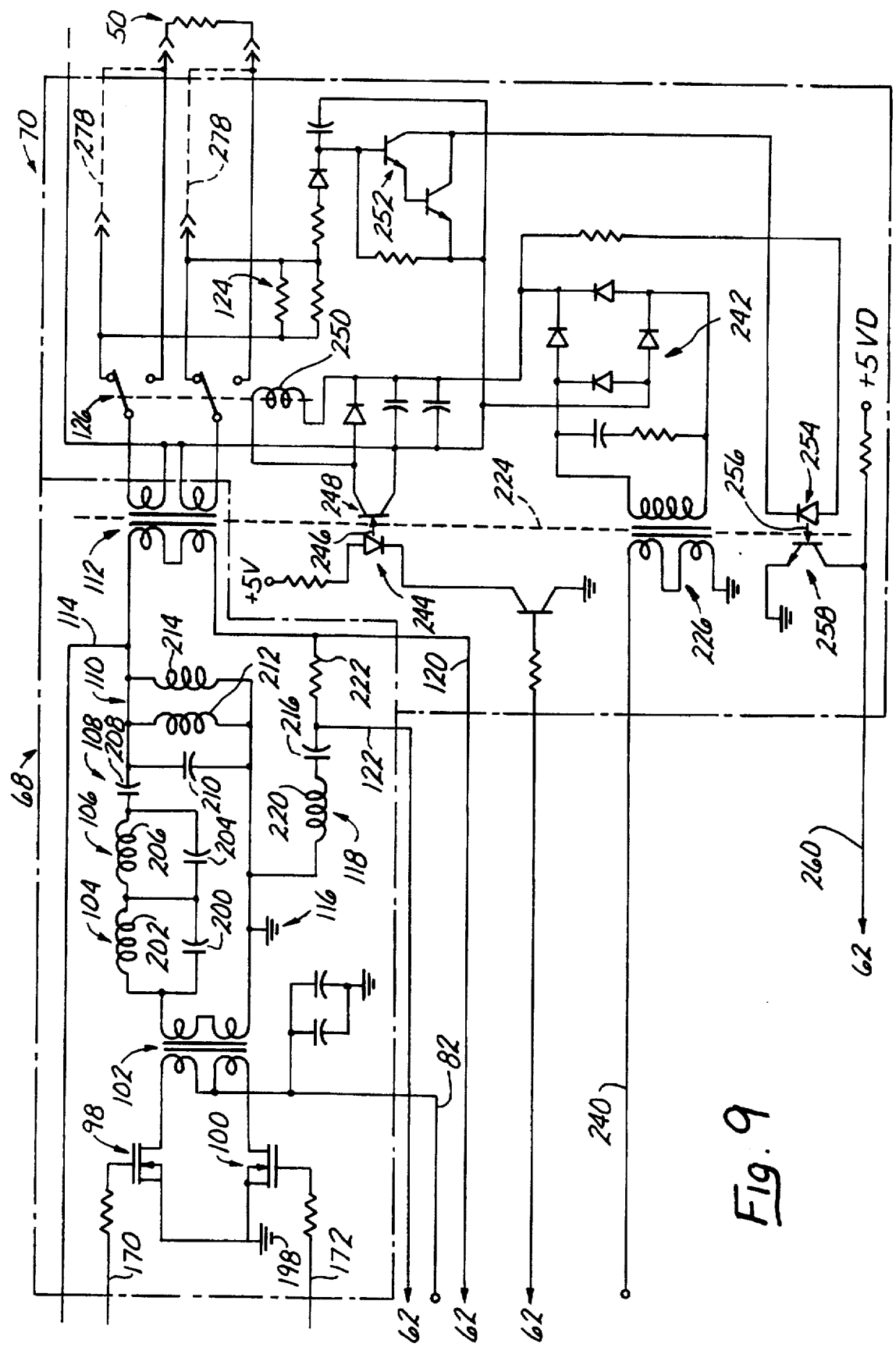

Viewing now FIG. 9, the power amplifier circuit section 68 and isolated patient-connected circuit section 70 are shown in greater detail. Recalling the description of the power amplifier circuit section 68, it is seen that this circuit section receives the signals of FIG. 5F on conductors 170 and 172. This circuit section also receives the selectively varied voltage output from voltage source circuit section 80 on conductor 82. The signals on conductors 170 and 172 drive MosFet switches 98 and 100 alternately into conduction, with the indicated dead time preventing simultaneous conduction of through these switches, so that the creation of a short from conductor 82 to ground connection 198 is prevented. The alternate current conduction through the switches 98 and 100 drives the center-tapped transformer 102 to provide an essentially symmetrical square wave output of 50 percent duty cycle into the first 300 KHz trap 104. This trap 104 includes a capacitor 200 and inductor 202 which in combination are tuned to present a high impedance to a 300 KHz frequency. Similarly, the 500 KHz trap 106 includes a capacitor 204 and inductor 206 which in combination are tuned to provide a high impedance to a 500 KHz frequency. The 100 KHz series tuner 108 of FIG. 3, is formed by the interaction of the two inductors 104 and 106 in series with a capacitor 208. These components are tuned to present a low impedance to a 100 KHz frequency and a comparatively high impedance to higher order (i.e., the 7th, 9th, etc.) harmonics of the 100 KHz selected frequency). The shunt tuner 110 of FIG. 3 is actually formed by a capacitor 210, and a pair of parallel connected inductors 212, 214, which pass higher order harmonics (now of comparatively low energy level) to ground connection 116. Series tuner 118 is formed by the cooperation of a capacitor 218 and an inductor 220, allowing the selected 100 KHz frequency to reach ground 116 with little impedance. Accordingly, the primary winding of isolation transformer 112 receives essentially alternating current power of essentially pure sine wave characteristic. It will be noted that the voltage drop occurring across a resistor 222, which is exposed essentially only to the selected 100 KHz frequency of the electrical power delivered into the resistive load 50 is available to the microprocessor 58 via the interface connections 62 bridging this resistor. Accordingly, the microprocessor 58 can verify when and if electrical power of the selected frequency is being delivered to heater 50 of catheter 16.

In order to further understand the control and safeguard features of the present invention, it should be noted that at the isolation transformer 112, is established a virtual isolation barrier, indicated with the dashed line 224. To the right hand side of the barrier 224 is the isolated patient connected portions of the power amplifier circuit 60, module 40, and catheter 16, with heater 50. No physical electrical connection is effected across the barrier 224. In order to control the relay 126, an additional isolation transformer 226 is provided. This isolation transformer is powered by a 100 KHz power supply circuit 228 seen on FIG. 4. Viewing the power supply circuit 228 on FIG. 4, it is seen that a divider 230 receives the signal of FIG. 5A from the oscillator 88, and is connected just like the divider 90 to provide a signal like that illustrated by FIG. 5C to a transistor 232. The transistor 232 toggles on and off in response to the signal from the divider 230, and similarly causes a second transistor 234 to toggle on and off. This second transistor 234 drives a pair of oppositely connected PNP (236) and NPN (238) transistors. The transistors 236 and 238 toggle on and off in opposition to one another to provide a low-power 100 KHz alternating current power supply at conductor 240.

Returning to FIG. 9, it is seen that the conductor 240 delivers this low-power 100 KHz alternating current power to the primary winding of the transformer. Thus, the same frequency of alternating current power which has been determined to offer the greatest level of patient safety is used to effect control of the isolated patient-connected circuit section 70. The secondary winding of transformer 226 drives a rectifier 242 providing direct current power on the isolated patient-connected circuit section 70. In order to control the relay 126, the microprocessor 58 can command illumination of a light emitting diode 244. Light from this LED (arrow 246) crosses the barrier 224, and causes a photodiode 248 to become conductive. The photodiode 248 controls current flow through the coil 250 of the relay 126 so that this relay is under the control of the microprocessor 58 with no physical connection across the barrier 224.

In order to inform the microprocessor 58 that power is being dissipated on the isolated patient-connected side of the barrier 224, the voltage drop occurring across the calibration resistor 124 is used to drive a transistor switching circuit into conductivity. It will be noted that the calibration resistor 124 is in fact formed by two resistors connected in parallel. Conductivity at switching circuit 252 illuminates a LED 254. Again, light from the LED 254 is beamed across the barrier 224 (arrow 256), and causes a photodiode 258 to become conductive. Conductivity of the photodiode 258 pulls low the signal on conductor 260, which has connection with the microprocessor 58, as is indicated by interface arrow 62.

Returning to a consideration of FIG. 3, it is seen that the microprocessor 58 has control over the relay 74, from which power is received to operate the entire power amplifier 60. In the event that the microprocessor 58 is informed that electrical power is being dissipated into the isolated patient-connected section 70 when this power dissipation has not been commanded, then the relay 74 will be opened to shut down the power amplifier. On the other hand, if after commanding the voltage source 80 (regulator 174) to provide a selected level of voltage and the closing of the relay 126, the microprocessor is not informed within a selected time interval (only a fraction of a second) that power is being dissipated in the isolated patient-connected section 70, then a fault is assumed. In this event also, the relay 74 will be opened, or the voltage regulator 174 is alternatively commanded to provide a zero voltage output, and the patient is protected from any and all inadvertent injury which might result from operation of the heating element 50 in the pulmonary artery 14 without adequate control.

Figure 10:
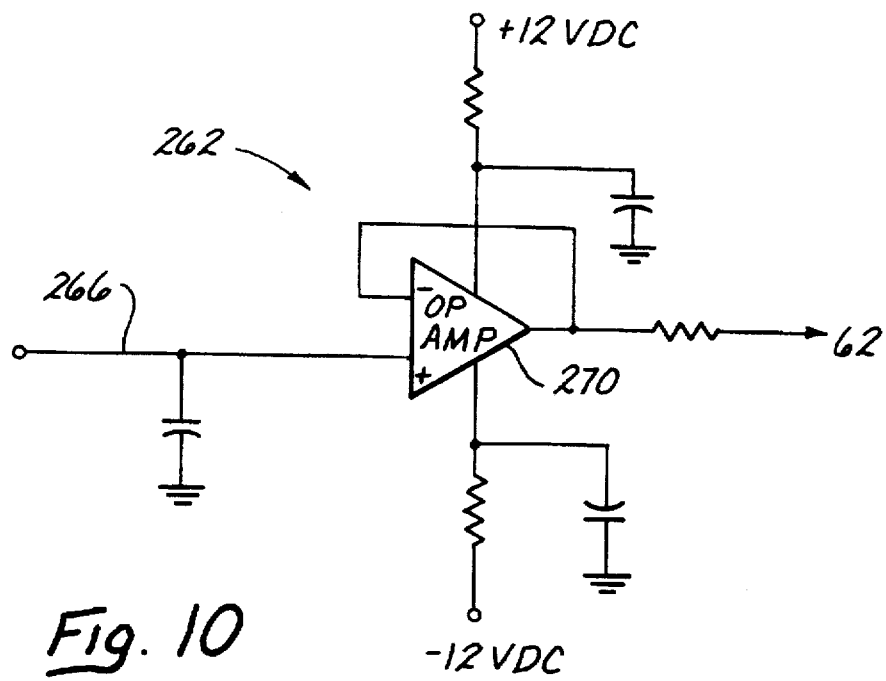
Figure 11:
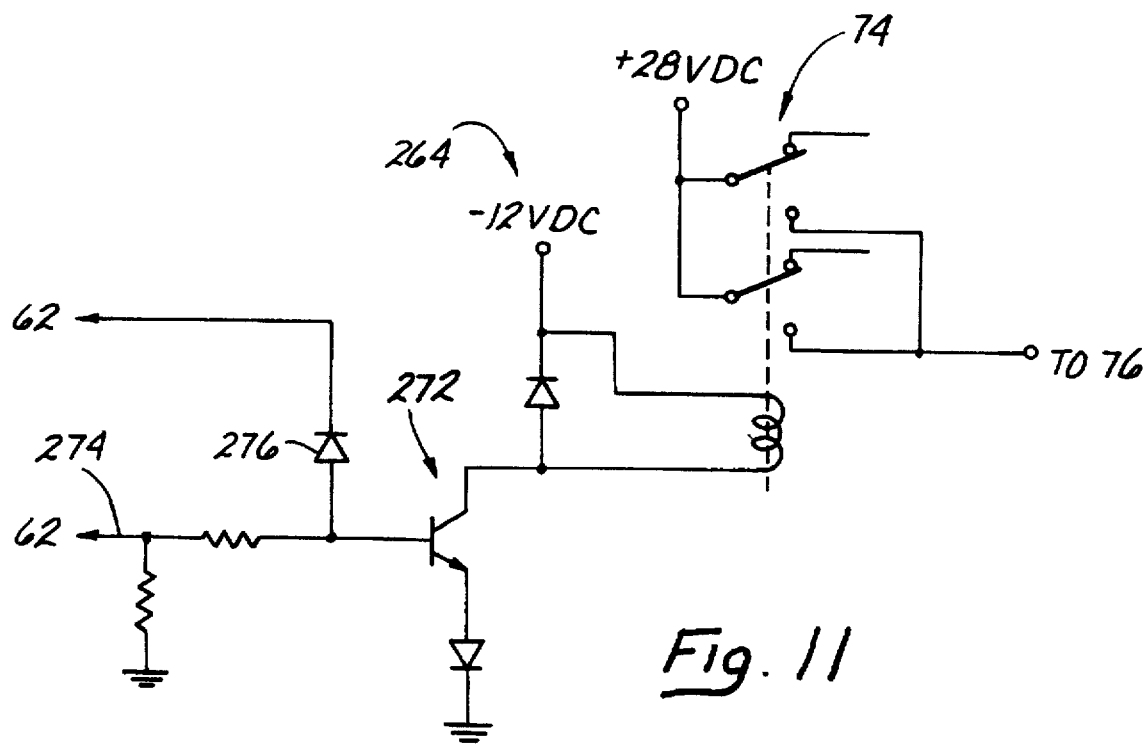

In order to provide the desired degree of safeguarding over unintended or inadvertent operation of the heating element 50, the power amplifier circuit 60 includes the circuit sections 262 and 264, which are illustrated in FIGS. 10 and 11, respectively. Particularly viewing the circuit portion 262, it is seen that the conductor 266 is seen in FIG. 7 to be connected to the regulated voltage output of the voltage source 174 at conductor 82 via a pair of voltage dividing resistors indicated with the numeral 268. The voltage level appearing at the conductor 266 is an indication of the voltage level actually provided by the voltage regulator 174. This voltage level is provided to a unitary gain buffer 270. This buffer 270 is an operational amplifier which provides an output to the microprocessor 58, indicated with the general interface numeral 62. Accordingly, the microprocessor 58 can read the voltage level provided by the voltage source 80 using voltage regulator 174. In the event that a fault in the regulator 174 or some other portion of the power amplifier 60 causes a voltage other than an acceptable and expected value to appear from the buffer 270, then the microprocessor 58 will effect a shutdown of the power amplifier 60.

Turning now to FIG. 11, the circuit section 264, which effects control of the relay 74 (recalling FIG. 3), is depicted. The circuit section 264 includes the relay 74 itself, and a transistorized switching circuit indicated with the numeral 272. This transistorized switching circuit 272 places the relay 74 under the control of the microprocessor via an interface effected by conductor 274. That is, a signal-high value at the conductor 274 provided by the microprocessor 58 will result in the switch circuit 272 closing and in the closing of the relay 74 to power the power amplifier 60. However, this closing of the switching circuit 272 can be effected only so long as the validity of this action is verified by an internal watch dog timer (not shown), which is associated with the microprocessor 58. In other words, if an internally repeated diagnostic of the microprocessor 58 is not successfully completed, the watch dog will reset and reboot the microprocessor 58 and will effect a shut down of the power amplifier 60 by pulling the signal on conductor 274 signal-low. This pull down of the signal on conductor 274 is effected through the diode 276, which has connection to the watch dog portion of the microprocessor 58 as is indicated by the interface numeral 62.

Turning once again to FIG. 1, it will be recalled that the module 40 includes provision to verify the correct functioning of the cable 30. That is, the cable 30 could be damaged during use of the monitoring apparatus including console 32, catheter 16, module 40 and cable 30. The console 32 and module 40 are durable components, while the catheter 16 is a single use apparatus. Consequently, a new catheter 16 is used with each patient. However, the cable 30, although it is a durable component is by far the most subject to damage from rough use, or by being stepped on, for example, in the medical treatment use environment for the apparatus described. In order to test and verify correct operation of the cable 30, the connector portion attached to the cable 30 at the plug-and-socket connection 16'/30' is connected back into the module 40 at the connector 41 provided on this module 40.

FIG. 9 illustrates with dashed lines 278 the electrical configuration effected by this connection of the cable 30 back into connector 41. In other words, with the cable 30 connected into connector 41, the resistance heating element 50 of a catheter 16 is not connected to the output of the relay 126. However, the calibration resistors 124 are still connected at the contacts of this relay 126 to which they ordinarily connect, and are also now connected via cable 30 to the contacts of this relay at which the resistance heating element 50 of the catheter 16 is connected in the use configuration of the apparatus. Consequently, with the cable 30 connected to the connector 41, if the console 32 is used to effect a calibration of the module 40 and catheter 16, the module 40 will read the calibration resistors 124 in the calibration sequence, and then will read these calibration resistors 124 again via the cable 30 as though it were testing the operational readiness of a catheter. In this test sequence, if there is more than a predetermined difference in resistance between the calibration resistors 124 and the heating resistor 50 of a catheter, the module 40 will signal via console 32 that the catheter is bad. However, in the cable test configuration described, this "bad catheter" signal will mean that the cable 30 itself is defective.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. A power amplifier circuit for receiving both electrical power in the form of direct-current and a frequency signal in the form of time-sequenced mirror-image square waves having a 50 percent duty cycle, and providing an essentially pure sinusoidal output voltage and current signal to an electrical load having resistive qualities, said power amplifier circuit comprising:

a pair of power-switching switches; and a transformer having a center-tapped primary winding, each of said pair of power-switching switches connecting to a respective opposite side of the primary winding of said transformer and receiving one of said time-sequenced mirror-image square waves of said frequency signal, in response to said frequency signal said power-switching switches switching said direct-current power through respective opposite sides of the primary winding of said center-tapped transformer;

a trap circuit connecting to the secondary winding of said center-tapped transformer and blocking at least the first odd-numbered harmonic frequency multiple of said frequency signal;

a series tuner circuit receiving electrical power from said trap circuit and allowing essentially unrestricted passage of a frequency matching said frequency signal;

a high-order shunt tuner circuit receiving electrical power from said series tuner circuit and shunting higher-ordered multiples of the frequency of said frequency signal.

2. The power amplifier circuit of claim 1 further including an isolation transformer having a primary winding receiving electrical power from said high-order shunt tuner circuit and a secondary winding providing electrical power to said electrical load, said primary winding having an effective impedance equal to a resistance value of said electrical load multiplied by the square of the turns ratio across said isolation transformer, and another series tuner circuit connecting to a side of said primary winding opposite to said series tuner circuit and allowing essentially unrestricted passage of a frequency matching said frequency signal; whereby the effective impedance value of said isolation transformer primary winding prevents aggregation of said series tuner and said another series tuner into a series tuner having a characteristic frequency other than the frequency of said frequency signal.

* * * * *